United States Patent
Fiehler

(12)
(10) Patent No.: US 6,238,578 B1
(45) Date of Patent: May 29, 2001

(54) METHOD FOR DISPENSING SEPARATOR GEL IN A BLOOD COLLECTION TUBE

(75) Inventor: William R. Fiehler, St. Louis, MO (US)

(73) Assignee: Sherwood Services AG, Schaffhausen (CH)

(*) Notice: Subject to any disclaimer, the term of this patent is extended or adjusted under 35 U.S.C. 154(b) by 0 days.

(21) Appl. No.: 08/762,358

(22) Filed: Dec. 9, 1996

(51) Int. Cl.[7] ............................. B01D 21/26; B05D 7/22
(52) U.S. Cl. ...................... 210/787; 210/513; 210/516; 210/789; 427/236
(58) Field of Search ............................ 210/513, 516, 210/518, 782, 789, 787; 435/2; 427/236; 118/52, 55, 232

(56) References Cited

U.S. PATENT DOCUMENTS

| | | |
|---|---|---|
| 3,516,385 * | 6/1970 | Walling . |
| 3,799,342 | 3/1974 | Greenspan ........................ 210/359 |
| 3,852,194 | 12/1974 | Zine, Jr. . |
| 3,901,219 | 8/1975 | Kay . |
| 3,902,964 | 9/1975 | Greenspan . |
| 3,919,085 | 11/1975 | Ayres . |
| 3,920,549 | 11/1975 | Gigliello et al. . |
| 3,976,579 * | 8/1976 | Bennett ............................ 210/789 |
| 3,977,982 | 8/1976 | Hertl . |
| 4,021,340 | 5/1977 | Zine, Jr. . |
| 4,043,295 | 8/1977 | Speck et al. . |
| 4,043,928 | 8/1977 | Lukacs . |
| 4,049,692 | 9/1977 | Zine, Jr. . |
| 4,140,631 | 2/1979 | Okuda et al. . |
| 4,153,739 | 5/1979 | Kessler . |
| 4,180,465 | 12/1979 | Murty ................................ 210/516 |
| 4,189,382 | 2/1980 | Zine, Jr. . |
| 4,190,535 | 2/1980 | Luderer et al. . |
| 4,246,123 * | 1/1981 | Cornell et al. ..................... 210/789 |
| 4,257,886 | 3/1981 | Kessler ............................ 210/516 |

(List continued on next page.)

FOREIGN PATENT DOCUMENTS 0 535 810    4/1993 (EP) .

*Primary Examiner*—John Kim
(74) *Attorney, Agent, or Firm*—Mark S. Leonardo; Peter B. Sorell; Brown Rudnick Freed & Gesmer

(57) ABSTRACT

A method of dispensing gel for separation of the serum and coagulum portions of a blood sample in a blood collection tube is disclosed. The present invention of dispensing the gel preferably comprises utilizing a gel dispensing apparatus with a nozzle head having a plurality of openings. The gel dispensing apparatus dispenses either a continuous band of gel around the central portion of the collection tube or a plurality of discrete stripes that forms a circumferential pattern thereto. Once the gel is dispensed, the tube is ready for accepting a blood sample for eventual separation in a centrifuge where the dispensed gel will form a barrier that exhibits strong adhesive properties after separation of the blood sample has occurred.

7 Claims, 3 Drawing Sheets

U.S. PATENT DOCUMENTS

| | | | |
|---|---|---|---|
| 4,308,232 | 12/1981 | Crouther et al. | 422/102 |
| 4,310,430 | 1/1982 | Ichikawa et al. | 252/60 |
| 4,386,003 | 5/1983 | Fiehler | 252/60 |
| 4,420,517 | 12/1983 | Ali | 428/35 |
| 4,426,290 | 1/1984 | Ichikawa et al. | 210/516 |
| 4,438,209 | 3/1984 | Mosier | 436/542 |
| 4,440,350 | 4/1984 | Dietz et al. | |
| 4,455,377 | 6/1984 | Finnerty et al. | 436/69 |
| 4,481,987 | 11/1984 | Burns | |
| 4,499,118 * | 2/1985 | Dietz et al. | 427/236 |
| 4,529,614 | 7/1985 | Burns | |
| 4,529,711 | 7/1985 | Fukano et al. | 436/177 |
| 4,579,828 | 4/1986 | Ali | |
| 4,620,549 | 11/1986 | Nugent | |
| 4,640,785 | 2/1987 | Carroll et al. | 210/782 |
| 4,707,276 * | 11/1987 | Dodge et al. | 210/789 |
| 4,711,820 | 12/1987 | Arkles et al. | 428/429 |
| 4,735,832 | 4/1988 | Ichikawa et al. | 428/35 |
| 4,770,779 | 9/1988 | Ichikawa et al. | 210/516 |
| 4,786,603 | 11/1988 | Wielinger et al. | 436/69 |
| 4,803,153 | 2/1989 | Shibata et al. | 435/2 |
| 4,808,449 | 2/1989 | McAlister | |
| 4,816,168 | 3/1989 | Carrol et al. | 210/782 |
| 4,836,987 | 6/1989 | Shibata et al. | 422/101 |
| 4,856,533 | 8/1989 | Anraku et al. | |
| 4,867,887 | 9/1989 | Smith | 210/782 |
| 4,890,627 | 1/1990 | Haber et al. | |
| 4,917,801 | 4/1990 | Luderer et al. | 210/516 |
| 4,957,638 | 9/1990 | Smith | 210/782 |
| 4,985,026 * | 1/1991 | Kasai et al. | 604/403 |
| 5,019,243 * | 5/1991 | McEwen et al. | 210/90 |
| 5,053,048 * | 10/1991 | Pinchuk | 604/266 |
| 5,053,134 * | 10/1991 | Luderer et al. | 210/516 |
| 5,086,783 * | 2/1992 | Macors et al. | 128/765 |
| 5,118,428 * | 6/1992 | Sand et al. | 210/749 |
| 5,169,720 * | 12/1992 | Braatz et al. | 428/423.1 |
| 5,213,765 * | 5/1993 | Kasai et al. | 422/101 |
| 5,246,666 * | 9/1993 | Vogler et al. | 422/73 |
| 5,257,633 * | 11/1993 | Vogler et al. | 128/763 |
| 5,262,067 * | 11/1993 | Wilk et al. | 210/767 |
| 5,266,199 * | 11/1993 | Tsukagoshi et al. | 210/516 |
| 5,284,588 * | 2/1994 | Makowski et al. | 210/638 |
| 5,290,552 * | 3/1994 | Sierra et al. | 424/94.64 |
| 5,320,812 * | 6/1994 | Harper | 422/102 |
| 5,326,535 * | 7/1994 | Vogler et al. | 422/102 |
| 5,342,753 * | 8/1994 | Smith, Jr. | 435/2 |
| 5,378,431 * | 1/1995 | Vogler et al. | 422/73 |
| 5,399,318 * | 3/1995 | Mancilla et al. | 422/100 |
| 5,464,776 * | 11/1995 | Vogler et al. | 436/69 |
| 5,494,590 * | 2/1996 | Smith et al. | 210/782 |
| 5,505,853 * | 4/1996 | Satake | 210/516 |
| 5,511,558 * | 4/1996 | Shepard et al. | 128/760 |
| 5,853,600 * | 12/1998 | McNeal et al. | 210/789 |

* cited by examiner

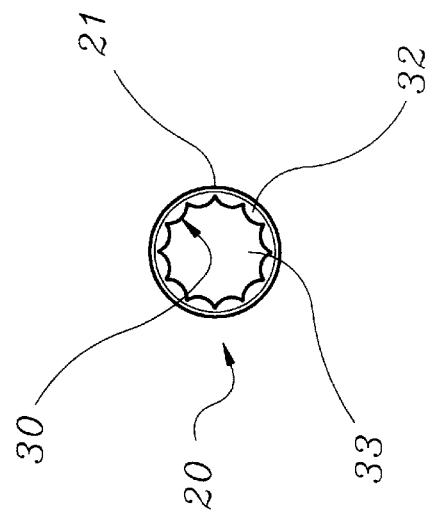
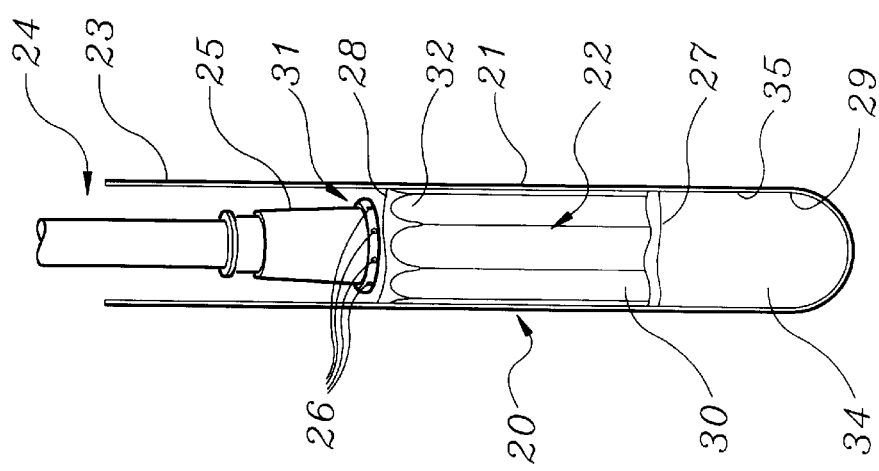

METHOD FOR DISPENSING SEPARATOR GEL IN A BLOOD COLLECTION TUBE

FIELD OF THE INVENTION

This invention relates generally to the method and apparatus for separating blood components in a blood collection device. Specifically, the invention relates to a method for the separation of the light serum portion of blood from the heavy cellular portion of blood, the blood collection device used to collect and separate the blood, and the method of manufacturing the blood collection device. More particularly, the invention relates to a method of dispensing separator gel in a blood collection tube for improving gel barrier stability and adhesion of the gel to the tube wall during the separation process.

PRIOR ART

Blood collection devices for separating the lighter serum portion of a blood sample from the heavier cellular portion thereof are well known. These devices usually comprise a collection tube containing a thixotropic gel and a contact activated clotting agent. The gel has a specific gravity intermediate the specific gravity of the serum and the cellular phases of the blood sample.

After a sample of blood has been deposited into the collection tube, the contact-activated clotting agents begin to clot the blood sample by activating clotting factors within the blood. The agent facilitates the clotting process until the blood is completely coagulated. It is essential that the agent coagulate substantially all of the blood sample in order for the subsequent serum separation process to be complete. Once the blood has coagulated, the collection tube is placed in a centrifuge to separate the lighter serum from the heavier coagulum portion. Coagulum is defined as the cellular portion and fibrin clot of the blood as opposed to the lighter serum portion of the blood. During centrifugation, the gel on the bottom of the collection tube is displaced upwardly through the blood sample until it reaches its equilibrium position at the interface between the serum and the coagulum. In this position, the gel forms a barrier between the serum and the coagulum which permits the lighter serum to be either decanted directly from the collection tube, or sampled using automated blood analyzing equipment, without interference from the coagulum.

It has long been known in the art that human blood can be readily centrifuged to effect a separation of the blood into its lighter serum and heavier coagulum portions. The specific gravity of the serum portion of human blood is between approximately 1.026 and 1.031, while the specific gravity of the coagulum portion of human blood is between approximately 1.092 and 1.095. The specific gravity of the gel is therefore chosen to be approximately between 1.032 and 1.091, so that once a blood sample is centrifuged, the gel will form an effective barrier between the serum and the coagulum. A preferred gel to be used with the method of the present invention is a thixotropic composition described in U.S. Pat. No. 4,140,631 to Okuda et al, entitled "Sealant for Separation of Serum or Plasma, and It's Use", the entire disclosure of which is hereby incorporated by reference. As described in Okuda et al., the preferred thixotropic gel is a polymer essentially consisting of at least one compound from the group of alkyl acrylates and alkyl methacrylates, which has a specific gravity of 1.03 to 1.08 and a viscosity of about 5,000 to 1,000,000 cps at a shear rate of 1 second$^{-1}$ when measured at 25° C. However, any suitable gel-like composition which can be used as a barrier between blood portions separated in a centrifuge is felt to fall within the spirit and scope of the present invention.

This type of gel is adapted to migrate or flow from the bottom of the tube under the influence of centrifugation to the interface position between the serum and the coagulum portions of the blood and adhere to the inside surface of the collection tube wall to form a barrier between the blood portions to maintain a separation therebetween. However, this migration causes an attendant loss of gel along the tube wall, thereby requiring initial placements of larger amounts of gel in the tube in order to insure the formation of a strong enough mechanical barrier to properly separate the two portions of blood during centrifugation.

Weak adhesion of the gel to the collection tube's inner surface during centrifugation of the blood sample is a problem with prior art blood collection devices. Such weak adhesion of the gel is due to the blood sample wetting the inner surface of the blood collection device prior to the migration of the gel. This wetted inner surface inhibits the natural adhesive properties of the gel, thereby preventing the gel from forming a strong adhesive bond thereto. U.S. Pat. No. 4,257,886 seeks to overcome this deficiency by disclosing a blood separation assembly that coats the bottom portion of the collection tube with a hydrophobic material that resists wetting of the collection tube's inner surface and allows the gel to form a strong adhesive bond to the inner surface during centrifugation.

Another method of addressing the gel migration problem with its attendant loss of adhesion is found in U.S. Pat. No. 4,417,981 (hereinafter the '981 patent) which attempts to overcome the problems associated with gel migration by dispensing the gel in a separator assembly located in the central portion of the collection tube near the eventual formation of the gel barrier. The pre-placement and dispensation of the gel in a separator assembly permits the gel to quickly adhere to the tube wall during centrifugation without migration and attendant loss of gel. However, the above method of dispensing gel using a device incurs further expense in manufacturing an additional element to attain proper separation of the blood sample.

Referring to FIGS. 1–4, the prior art method of dispensing separator gel 3 and separating a blood sample into two portions is shown. The method involves utilizing a commonly known gel dispensing apparatus (not shown) to dispense a predetermined amount of gel 3 into the bottom 5 of a collection tube 2. Contact-activated clotting powder or particles 6 are then deposited inside the collection tube 2 for eventual activation of clotting factors within blood 7 after blood 7 is added to the tube 2.

As shown in FIG. 2, a predetermined amount 4 of blood 7 is added to the collection tube 2 and the contact clot-activating material 6 within tube 2 begins to coagulate the blood 7 before the tube 2 is placed in a centrifuge (not shown) for centrifugation of the blood 7. The contact clot-activating material 6 promotes clot formation and includes but is not limited to glass and silica. Referring now to FIG. 3, during centrifugation of the blood 7 in the collection tube 2, the gel 3 becomes less viscous and begins to migrate upward along the tube's 2 inner surface 8 until it reaches an interface point 9 where the lighter serum portion 10 of the blood 7 begins to separate from the heavier coagulum portion 11. The interface point 9 is a result of the two portions of blood, serum 10 and coagulum 11, being physically separated due to the effect of their different specific gravities during centrifugation. As shown in FIG. 4, the separation gel 3, having a specific gravity intermediate that of the serum 10 and coagulum 11, has migrated to the interface point 9 between the two blood portions. At the interface point 9, the gel 3 forms a mechanical barrier 12 inside the collection tube 2 that physically separates the two blood portions and prevents the serum 10 from being contaminated by coagulum 11.

As of yet, nothing in the prior art has addressed the problem of developing an efficient means of dispensing gel that does not suffer from either attendant loss of gel caused by migration or weak adhesive properties when the gel barrier 12 is formed.

Therefore, there exists a need in the blood collection art for an improved means of dispensing gel into a collection tube in an inexpensive and efficient manner which promotes both quick formation of the barrier separating the two blood portions and strong adhesion of the barrier to the collection tube's inner surface once the gel barrier is formed.

SUMMARY OF THE INVENTION

In brief summary, the present invention relates to a means of dispensing gel for separation of the lighter serum portion and the heavier coagulum portion of a blood sample in a blood collection tube. The preferred method of dispensing the gel comprises utilizing a gel dispensing apparatus with a nozzle head or like portion having a plurality of openings. The gel dispensing apparatus dispenses either a continuous band of gel around the central portion of the collection tube or a plurality of discrete stripes that flow to form a continuous band pattern around the central portion of the collection tube. Once the gel is so dispensed about the central portion of the collection tube, the tube is ready for accepting a blood sample for eventual separation in a centrifuge where the dispensed gel will form a barrier between the serum portion and the coagulum portion of the blood sample while exhibiting strong adhesive properties, i.e., few to no points of fluid communication between blood portions.

The present invention includes a method of dispensing gel in a tube is claimed having opposed open and closed ends, a central body portion between the opposed open and closed ends, and an interior surface formed by the central body portion and the closed end, comprising the steps of: providing the tube providing a gel dispensing apparatus for dispensing a gel into the tube, placing a portion of the apparatus inside the tube, dispensing the gel from the portion of the apparatus onto an interior wall surface formed by the central body portion, and terminating the dispensation of the gel.

The present invention further includes a blood collection device for use in separating blood into different portions comprising a tube having a central body portion, opposed closed and open ends, and an interior surface with gel dispensed on an interior wall surface thereof. Optionally, contact clot activating particles may be placed within the device.

The present invention still further includes a method of separating blood into different portions using the aforementioned blood collection device optionally containing contact clot-activating particles comprising the steps of: placing a blood sample inside the blood collection device, centrifuging the device containing the blood sample wherein centrifuging the device and the blood sample permits the gel to flow inwardly from the interior wall surface to form a barrier between the different portions of the blood sample after centrifugation is completed.

Accordingly, a principal object of the present invention is to provide an efficient and inexpensive method for dispensing gel in a collection tube for use in separating a blood sample into portions.

Another important object of the present invention is to provide an improved method of dispensing gel that requires minimal or no migration of the gel along the tube wall to form a barrier between portions of blood being separated during centrifugation.

A further object of the present invention is to provide a method of dispensing gel that forms continuous and a stable barrier in a short period of time and exhibits strong adhesive properties, i.e., few to no points of fluid communication between the blood portions.

Another important object of the present invention is to provide a means of dispensing gel in discrete stripes or a contiguous band around the interior wall surface of a collection tube.

A further object of the present invention is to provide a blood collection device that has gel dispensed on the interior wall portion of a tube.

Another principal object of the present invention is to provide a method of using a tube with gel dispensed on the inner surface thereof for separation of blood into separate portions.

Additional objects, advantages and novel features of the invention will become apparent to those skilled in the art upon examination of the following more detailed description and drawings in which like elements of the invention are similarly numbered throughout.

BRIEF DESCRIPTION OF THE DRAWINGS

FIG. 5 shows the preferred present method of dispensing gel on the interior wall portion of a collection tube using a nozzle head for dispensing gel in a contiguous band around the interior wall portion of the collection tube;

FIG. 6 shows a top section view of the blood collection tube of FIG. 5 showing the gel on the inner surface of the tube with an opening therethrough.

DETAILED DESCRIPTION

Figure 1:
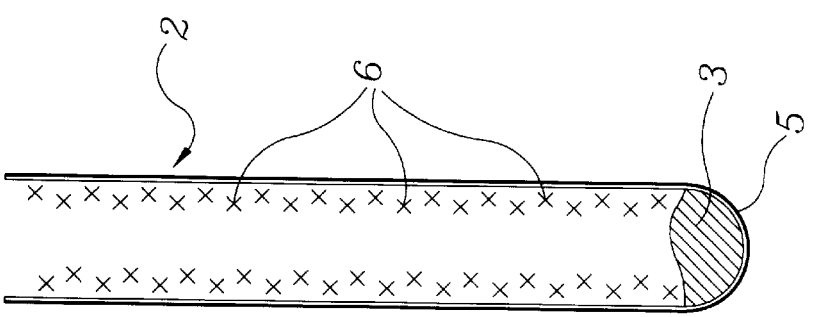
FIG. 1 shows the prior art method of dispensing gel at the bottom of a blood collection tube.
Figure 2:
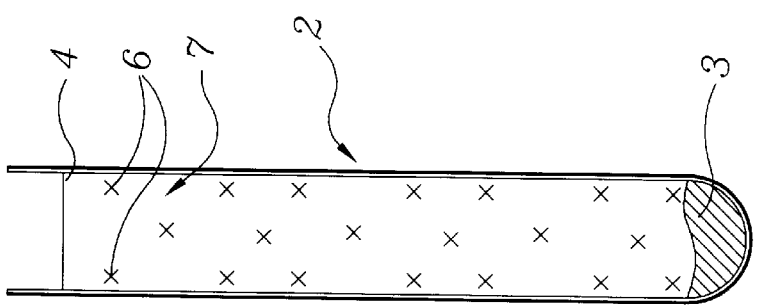
FIG. 2 shows the prior art blood collection tube of FIG. 1 after a blood sample has been added thereto.
Figure 3:
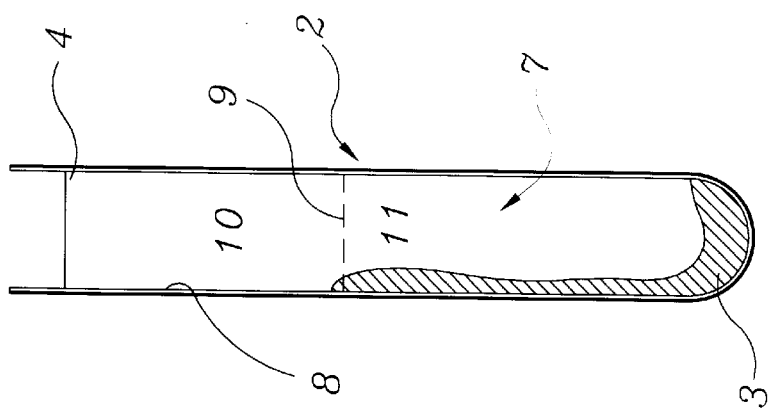
FIG. 3 shows the prior art migration of gel toward the serum/coagulum interface during centrifugation of the blood sample.
Figure 4:
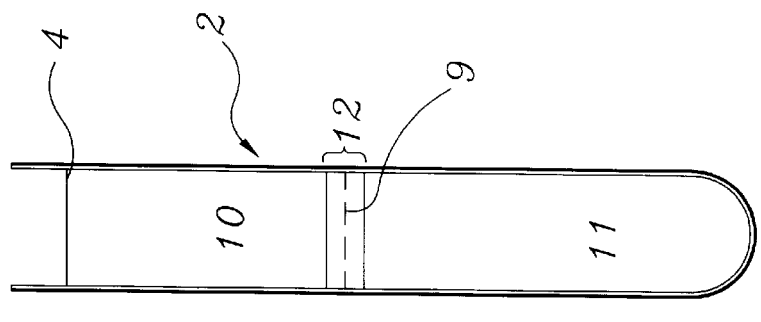
FIG. 4 shows the prior art blood collection tube after centrifugation of the blood sample and the formation of the gel barrier at the interface between the two portions of the blood.
Figure 8:
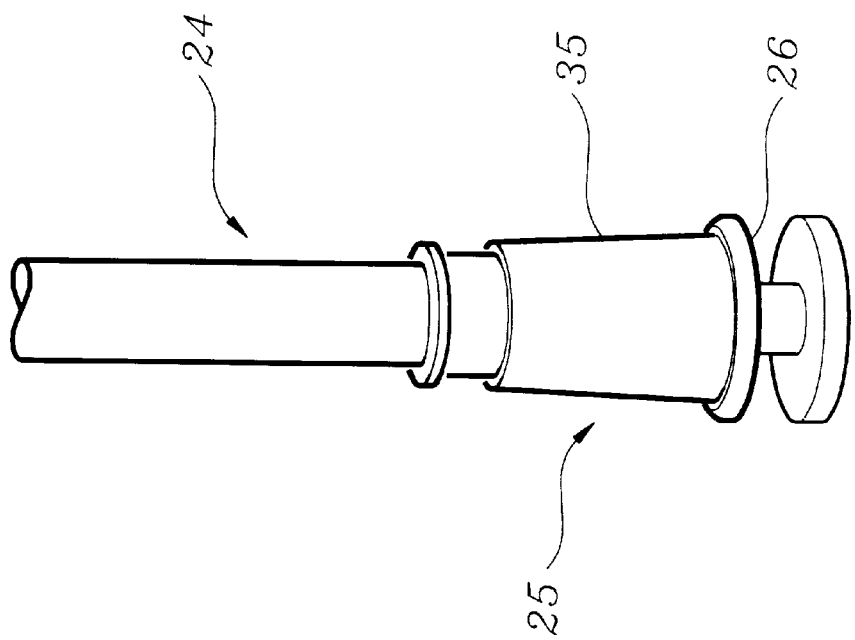
FIG. 8 is a perspective view of the gel dispensing apparatus showing the alternative embodiment of a continuous opening at the nozzle head.

In the preferred method of dispensing gel within a blood collection tube as illustrated in FIG. 5, a blood collection device 20, preferably a conventional collection tube 21 having an opposed open end 23 and closed end 34 is made of a material which is non-interactive with the blood 35, such as but not limited to plastic, glass, plastic-lined glass or glass-lined plastic. The collection tube 21 has separator gel 22 which is a thixotropic substance dispensed into the central portion of tube 21 between opposed open end 23 and closed end 34 prior to adding a blood sample 35. Gel 22 is placed within the tube 21 by using a positive displacement metering apparatus 24 that uses a nozzle head 25 for dispensing a gel or the like. The nozzle head 25 includes one or more openings but preferably a plurality of openings 26 located at its free distal end 31. If one opening is provided at the free distal end 31, the opening is preferably a continuous opening around the periphery of an exterior surface 35 of nozzle head 25 as illustrated in FIG. 8. Although one or more openings 26 can be utilized for the present invention, the preferred embodiment having a plurality of openings 26 will be exemplified throughout the remainder of this description for purposes of simplicity only. The plurality of openings 26 dispense the gel 22 onto the inner surface 29 of the tube 21 in discrete stripes 30 that flow to form a circumferential band pattern around tube 21. Preferably, the gel 22 is dispensed in discrete stripes 30, although any suitable configuration that ultimately flows to form one or more continuous bands 30 around the inner surface 29 of the collection tube 21 is felt to fall within the spirit and scope of the present invention.

Prior to dispensing gel 22, the nozzle head 25 is placed inside the collection tube 21 such that openings 26 are positioned at a predetermined lower point 27 to begin dispensing gel 22 along the inner wall surface 29 of tube 21. As gel 22 is dispensed through openings 26, the tube 21 is slowly drawn downward so as to move closed end 34 away from the nozzle head 25 until the openings 26 reach a predetermined upper limit 28 near open end 23. As the dispensing procedure is about to terminate, the nozzle head 25 is slightly ahead of the gel 22 flow, thereby forming a discontinuous circumferential pattern 32 at the predetermined upper limit 28. In the preferred method of dispensation with a plurality of openings 26, the discontinuous circumferential pattern 32 formed at the end of dispensation is a crown shape design, but any suitable pattern 32 may be made. Once the dispensation of the gel 22 is terminated, the gel 22 flows and adheres to the inner surface 29 forming a concentric band 30 around the central portion of tube 21 between the predetermined upper and lower limits, 28 and 27 respectively. As better seen in FIG. 6, the gel 22, after flow thereof has ceased, forms a concentric band 30 with the discontinuous pattern 32 at the top of band 30 and an opening 33 through which the blood sample 35 may initially pass before centrifugation and formation of the gel barrier. After the gel 22 has set or flow has ceased, the collection device 20 is ready for the blood sample 35 to be added for centrifugation and separation as described above.

Figure 7:
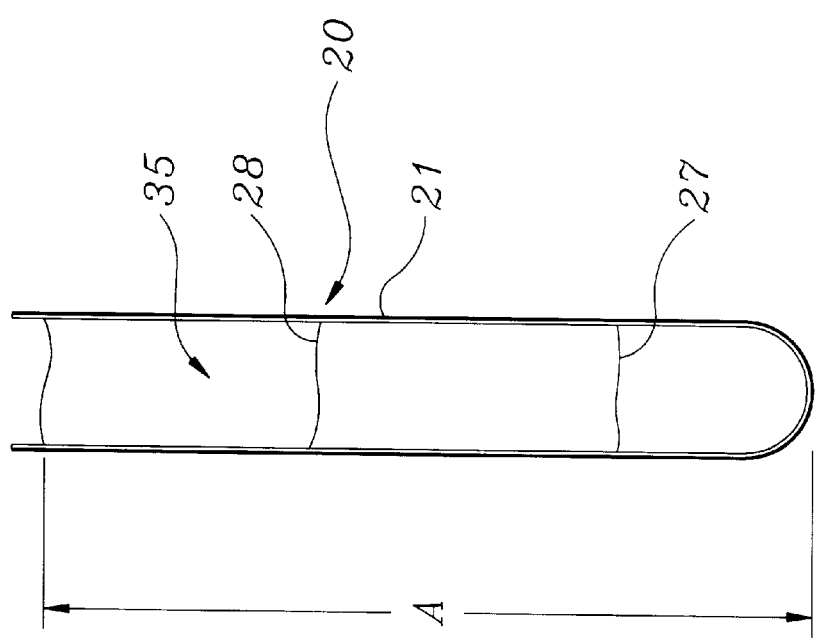
FIG. 7 shows the blood collection tube of the present invention demonstrating the method of determining the lower and upper limits for dispensing gel.

The location of the upper and lower limits, 28 and 27 respectively, in dispensing gel 22 to form a concentric band on the inner surface 29 of the collection tube 21 depends on the size of the tube 21 being utilized and the volume of the blood sample 35 to be added to the tube 21. Referring to FIG. 7, a general formula for determining the upper and lower limits, 28 and 27 respectively, for gel 22 dispensation will be discussed. X is a variable that represents the volume of the blood sample 35 added to the collection tube 21 prior to centrifugation. In determining the lower and upper limits for gel placement, 27 and 28 respectively, variable X is multiplied by predetermined constants, $C_{LL}$ for the lower limit 27 and $C_{UL}$ for the upper limit 28. These constants are established by one skilled in the art based on the for a particular size of the tube 20 and the particular gel configuration desired. The formulas used are shown below:

lower limit 27=$X \cdot C_{LL}$ upper limit 28=$X \cdot C_{UL}$

For example if $C_{LL}$ and $C_{UL}$ are established as being 0.7 and 0.31 respectively for a particular tube to achieve a particular desired configuration, the lower and upper limits, 27 and 28, respectively, may be easily determined by knowing the volume of the drawn blood sample 35 added to the collection tube 20. To illustrate, if a blood sample 35 having a volume of 100 mm is added to the collection tube 21, the lower limit 27 for dispensing gel 22 would be 70 mm and the upper limit 28 would be 31 mm as set forth below.

lower limit 27=100 mm×0.7=70 mm upper limit 28=100 mm×0.31=31 mm

Thus, the gel 22 would be dispensed between a range of 31 mm to 70 mm from the open end 23 to form a band 30. It should be noted that the formula would be varied accordingly if more than one band 30 would be desired for further separation techniques known in the art.

The above example is used for the purpose of illustrating the upper and lower limits, 28 and 27 respectively, for dispensing gel 22 in a collection tube 21 made according to the preferred embodiment of the present invention. The above formula insures that a firm mechanical gel barrier is formed after centrifugation regardless of the type of centrifuge used to separate the blood sample 35.

The preferred method of dispensing gel 22 as described above has the advantage of limited migration of the gel 22 during centrifugation while promoting a stronger mechanical barrier after centrifugation. Moreover, dispensing gel 22 on the interior wall portion between upper and lower limits, 28 and 27 respectively, of collection tube 21 has the further advantage of requiring less gel 22 than required in prior art methods in which gel 22 migration was utilized. For example, prior art methods for dispensing gel 22 dispense approximately 2.2 grams of gel 22 to form a sufficient barrier after centrifugation of the blood sample 35 while the present invention requires approximately 1.4 grams of gel 22 to form the same strong barrier. Thus the present invention requires approximately 36% less gel 22 which creates a significant cost savings.

Finally, the method of separating a blood sample 35 into different portions using the blood collection device 20 of the present invention will be discussed. The method of separating a blood sample 35 using the blood collection device 20 having contact clot-activating particles 6 previously deposited inside device 20 comprises the first step of providing a blood sample 35 inside the device 20. After the blood sample 35 is deposited, the sample 35 is then centrifuged, wherein centrifuging the blood sample 35 permits the gel 22 to flow inwardly as the blood sample 35 travels through the opening 33 until a barrier is formed between the different phases of the blood sample 35 once centrifugation is complete.

The blood collection device 20 of the present invention may likewise optionally contain contact clot-activating particles such as but not limited to carbon, silica, fumed silica, glass and the like. Likewise, the entire interior surface or a portion of the interior surface of the blood collection tube 21 of the present invention may optionally be sprayed with a water and/or silica mixture to prevent blood from sticking to the sides of the tube. This spray is preferably applied before dispensing of the gel 22 as described above.

Optionally, the interior of the blood collection device 20 of the present invention may be sprayed with an ethylene copolymer such as but not limited to polyethylene oxide and/or polydimethyl siloxane to promote gel 22 binding to the wall.

Although particular embodiments of the invention have been shown, it is not intended that the invention be limited thereby, instead the scope of the present invention is intended to be limited by the appended claims.

I claim:

1. A method of dispensing thixotropic gel in a tube having opposed open and closed ends, a central body portion between opposed open and closed ends, such that a lumen is defined, and an interior surface formed by said central body portion and said closed end, comprising the steps of:
   a) providing said tube for centrifuging a blood sample;
   b) providing a gel dispensing apparatus for dispensing the thixotropic gel into the tube, wherein said apparatus includes a plurality of openings through which gel is dispensed;
   c) placing a portion of said apparatus inside the tube;
   d) dispensing the thixotropic gel through said apparatus onto an interior wall surface formed by said central body portion, wherein said gel is dispensed in a plurality of discrete stripes;
   e) terminating dispensation of the gel;
   f) introducing a blood sample into said lumen; and
   g) centrifuging said tube containing said sample.

2. The method of dispensing gel according to claim 1, wherein said gel is dispensed in a band around said interior surface of said tube.

3. The method of dispensing gel according to claim 1, wherein said gel is dispensed in a plurality of discrete strips that flow to form a circumferential pattern on said interior wall surface.

4. A method of dispensing thixotropic gel in a tube having opposed open and closed ends, a central body portion between opposed open and closed ends, such that a lumen is defined, and a central body interior surface having a gel placement area defined by a specific upper limit and a specific lower limit, comprising the steps of:
   a) providing said tube for centrifuging a blood sample;
   b) providing a gel dispensing apparatus for dispensing the thixotropic gel into the tube;
   c) placing a portion of said apparatus inside the tube;
   d) dispensing the thixotropic gel through said apparatus onto said gel placement area of said central body interior surface, wherein said gel is dispensed in a plurality of discrete stripes;
   e) terminating dispensation of the gel;
   f) introducing a blood sample into said lumen; and
   g) centrifuging said tube containing said sample.

5. The method of dispensing gel according to claim 4, wherein said portion of said apparatus includes a plurality of openings through which said gel is dispensed.

6. The method of dispensing gel according to claim 4 wherein said step of dispensing the thixotropic gel through said apparatus onto said gel placement area of said central body interior surface and said step of terminating dispensation of the gel are performed prior to the step of introducing a blood sample into said lumen and the step of centrifuging said tube containing said sample.

7. The method of dispensing thixotropic gel according to claim 4 wherein said gel placement area is a concentric band.

* * * * *